United States Patent [19]

Thomas et al.

[11] 4,111,684

[45] Sep. 5, 1978

[54] HERBICIDE-FILLED CELLULOSE ESTER PARTICLES HAVING CONTROLLED RELEASE PROPERTIES

[75] Inventors: Norman W. Thomas, Warren; Frank S. Model, Basking Ridge; Charles L. Smart, Millington, all of N.J.

[73] Assignee: Celanese Corporation, New York, N.Y.

[21] Appl. No.: 791,823

[22] Filed: Apr. 28, 1977

[51] Int. Cl.$^2$ .......................... A01N 9/24; A01N 9/20
[52] U.S. Cl. ........................... 71/115; 71/64 F; 71/DIG. 1
[58] Field of Search ................. 71/DIG. 1, 115, 64 F

[56] References Cited

U.S. PATENT DOCUMENTS

| | | | |
|---|---|---|---|
| 3,013,873 | 12/1961 | Hart et al. | 71/111 X |
| 3,014,063 | 12/1961 | McLane et al. | 71/111 X |
| 3,172,752 | 3/1965 | Pierce | 71/65 X |
| 3,318,769 | 5/1967 | Folckemer | 424/81 X |
| 3,328,256 | 6/1967 | Gaunt | 71/DIG. 1 |
| 3,336,155 | 8/1967 | Rowe | 8/29 X |
| 3,560,196 | 2/1971 | Horai et al. | 71/115 |

OTHER PUBLICATIONS

Stokes et al., J. Agr. Food Chem., vol. 21, 1973, pp. 103–108.

*Primary Examiner*—Joseph Paul Brust

[57] ABSTRACT

A water-leachable herbicide occupies the voids, or channels, of a particulate, substantially water-impermeable porous cellulose ester carrier which provides controlled release of the herbicide into soil.

The herbicide-filled cellulose ester composition can be prepared by the method which comprises:

(a) dissolving cellulose ester in a solvent;

(b) combining the cellulose ester solution with a sufficient amount of a liquid which is a non-solvent for cellulose ester, but miscible with the cellulose solvent, under vigorous agitation to provide a homogeneous liquid containing porous cellulose ester particles having voids, or channels, communicating with the exterior surface thereof;

(c) contacting the cellulose ester particles with a water-leachable herbicide dissolved in a liquid which is a non-solvent for cellulose ester whereby the voids, or channels, of the cellulose ester particles become partially or substantially completely occupied with at least part of the herbicide solution; and (d) drying the cellulose ester particles.

The herbicidal composition can also be prepared by the leaching and pulverizing method fully disclosed in the description of the preferred embodiments herein.

13 Claims, No Drawings

HERBICIDE-FILLED CELLULOSE ESTER PARTICLES HAVING CONTROLLED RELEASE PROPERTIES

BACKGROUND OF THE INVENTION

1. Field of the Invention

This invention relates to the field of water-leachable pre-emergence herbicidal compositions which are characterized by controlled release of the herbicide contained in the composition on exposure to moisture.

2. Description of the Prior Art

Herbicides are substances used to destroy plants, especially weeds, or to check their growth. Commonly, for weed control in agriculture, water soluble herbicides are employed in the soil to prevent the emergence of undesired plants, e.g. weeds, which compete with desired plants. Such herbicides are referred to as pre-emergence herbicides and are usually dependent on rain or irrigation to wash the herbicide into the soil. Due to variable rainfall, the efficiency of washing such herbicides into the soil poses a difficult problem in that with increased rainfall the extent of penetration into the soil layer by the herbicide may be excessive with highly soluble herbicides, i.e., the herbicide is leached to a zone below that in which the undesired, i.e., weed seeds are germinating. The result is an unsatisfactory weed control. In addition to the solubility problem, penetration differentials are also attributable to the type of soil, i.e., sandy, loose soil versus muck soil, and importantly, the relative ability of the soil components to absorb the herbicide. It is apparent that the success of weed control among agricultural crops such as beans and tomatoes with pre-emergence herbicides is a complex problem which must entail consideration of the soil, crop, weed and environmental conditions, especially rainfall.

In addition to the problem of leaching the herbicide to below the zone of weed seed germination, is the problem generated by excessively long residence time of the herbicide in the upper zones of the soil where, on a protracted basis, adverse effects of the herbicide can occur with respect to the germination of desired seeds, or alternatively, with respect to established plants or trees. Thus, the leachability of the herbicide must permit adequate penetration to the soil zone where weed seeds are germinating but at the same time should be sufficient to remove the herbicide from the growth zone within reasonable periods of time. Ideally, the herbicide should have a leachability which would permit effective presence only during the germination period of the undesired seeds, after which the herbicide is effectively removed from the growth zones of the soil.

Amiben is a known pre-emergence herbicide which is of high water solubility. This commercial product, however, suffers from the aforesaid difficulties when employed in the soil, primarily because of water-solubility, i.e., heavy rain may leach the herbicide below the zone of weed seed germination. Amiben also is not as readily absorbed by the soil as are other pre-emergence herbicides, in which event the leaching rate of Amiben in sandy soil and clay loam soil is substantially the same, as evidenced by the relatively small changes in leaching rates required to obtain similar weed control in both sandy and clay loam soil. Even in muck soil, Amiben appears to move rather readily through the soil profile. Other herbicides, such as Diuron CIPC and PCP require several fold changes in rate to produce similar herbicidal effect with broad changes in the soil types. It is suggested the Amiben, when absorbed, is more strongly absorbed than other herbicides, but it remains that Amiben is not absorbed to any appreciable degree by soil constituents.

Attempts to effect control of leaching of Amiben have taken several approaches. Salt formation with metals such as barium, aluminum and iron did not appreciably vary field performance, presumably because the salts reach an equilibrium with naturally occurring cations in the soil. Since Amiben is a substituted benzoic acid, amides and esters were prepared and found to have major differences in leaching characteristics. Such derivatives, however, require water to hydrolyze the derivative for effectiveness.

In U.S. Pat. No. 3,560,196, it is proposed to combine Amiben, inter alia, with a granular carrier coated with a silicate binder which binder is treated to render it partically insoluble. The rate of release of the biologically active material is principally dependent on the silicate binder, more specifically the relative insolubility of the silicate binder.

U.S. Pat. No. 3,336,155 describes the coating of solid and liquid particles with polymers separated from an organic solvent solution thereof by the addition, under stirring, of an organic liquid which is a non-solvent for the polymer, but is miscible with the polymer solvent, and the solid or liquid particles which must be insoluble in the miscible solvent and nonsolvents. Among the numerous polymers and materials to be coated recited in U.S. Pat. No. 3,336,155 are cellulose acetate and the water soluble herbicide, sodium (2,4-dichlorophenoxy) acetate.

U.S. Pat. No. 3,318,769 describes a thermoplastic resin such as cellulose acetate having dissolved therein up to about 70% by weight of a dialkyl beta-halogen substituted vinyl phosphate insecticide. These water insoluble insecticides evaporate into the surrounding atmosphere over an extended period.

The benzoic acid pre-emergence herbicides are well known compounds and have been described in the patent literature (See U.S. Pat. Nos. 3,013,873 and 3,014,063).

Amiben is particularly characteristic of the benzoic acid-herbicides which are especially affected by water solubility and, consequently, the problem of excessive leaching by water, e.g. rainfall, in the soil. The known class of benzoic acid herbicides includes mono-, di-and tri-substituted benzoic acids, in which the substituents are halo, amino, nitro and lower alkoxy. The most effective of such derivatives are the tri-substituted benzoic acid herbicides, particularly those containing chloro substituents, most preferably at least two chloro substituents. Thus, Amiben is 3-amino-2,5-dichlorobenzoic acid (U.S. Pat. No. 3,013,873); Banvel, another commercial herbicide is 2-methoxy-3,6-dichlorobenzoic acid. Other such herbicides include, for example, trichlorobenzoic acid; 3-nitro-2,5-dichlorobenzoic acid (Dinoben) and similar such tri-substituted benzoic acids.

SUMMARY OF THE INVENTION

It has now been very surprisingly discovered that compositions of water-leachable herbicide in a matrix of cellulose ester ameliorates the problem of excessive leaching by water while still providing effective levels of the herbicide for control of undesired seed germination as well as weed growth after germination. The present discovery is indeed surprising since the cellulose ester of the present composition does not undergo decomposition under the conditions of use of the compositions as a prerequisite for release of the active herbicide contained therein, which is normally the manner in which so-called sustained-release formulations operate. In actual use, the cellulose ester appears to undergo no substantial change during the period when the herbicide acts on the ambient soil.

The controlled release obtainable with the present new compositions provides desirable levels of the herbicide in the ambient soil to provide significant herbicidal action, at the same time minimizing the undesirable leaching of the herbicide by soil water. In addition to obvious benefits, the present new compositions minimize the danger of contamination of underground water supplies by significant levels of the herbicide. The results obtained with Amiben, a widely used benzoic acid herbicide, are quite remarkable. Comparable controlled release is obtained with other benzoic acid herbicides.

Broadly stated, the herbicidal composition of the present invention comprises discrete particles of water-leachable herbicide occupying the voids, or channels, of a particulate, substantially water-impermeable, porous cellulose ester carrier, said voids, or channels communicating with the exterior surface of the carrier particles.

The herbicidal composition can be prepared by the solvent separation method which comprises:
(a) dissolving cellulose ester in a solvent;
(b) combining the cellulose ester solution with a sufficient amount of a liquid which is a non-solvent for cellulose ester, but miscible with the cellulose solvent, under vigorous agitation to provide a homogeneous liquid containing porous cellulose ester particles having voids, or channels, communicating with the exterior surface thereof;
(c) contacting the cellulose ester particles with a water-leachable herbicide dissolved in a liquid which is a non-solvent for cellulose ester whereby the voids, or channels, of the cellulose ester particles become partially or substantially completely occupied with at least part of the herbicide solution; and
(d) drying the cellulose ester particles.

Alternatively, the herbicidal composition can be prepared by the method which comprises:
(a) incorporating particles of a solid foreign material insoluble in cellulose ester substantially uniformly throughout a mass of cellulse ester;
(b) pulverizing the cellulose ester mass to provide cellulose ester particles containing particles of solid foreign material distributed substantially uniformly throughout said particles;
(c) leaching the particles of solid foreign material contained in the cellulose ester particles with a liquid which is a solvent for the foreign material but a non-solvent for the cellulose ester to provide porous cellulose ester particles having voids, or channels, communicating with the exterior surface of said particles;
(d) contacting the cellulose ester particles with a water-leachable herbicide dissolved in a liquid which is a non-solvent for cellulose ester whereby the voids, or channels, of the cellulose ester particles become partially or substantially completely occupied with at least a part of the herbicide solution; and
(e) drying the cellulose ester particles.

It is also within the scope of this invention to leach the particles of solid foreign material from the cellulose ester mass prior to the pulverization of the latter.

DESCRIPTION OF THE PREFERRED EMBODIMENTS

The preferred water-leachable herbicides for use herein are the benzoic acid herbicides containing at least two halogen substituents on the benzene ring with a third substituent which can be halogen, lower alkoxy, nitro or amino. The preferred halogen is chlorine. Representative preferred herbicides are:
3-nitro-2,5-dichlorobenzoic acid (Dinoben)
3-amino-2,5-dichlorobenzoic acid (Amiben)
2-methoxy-3,6-dichlorobenzoic acid (Banvel)
2,4,6-trichlorobenzoic acid
2,3,6-trichlorobenzoic acid More than one such herbicide can be present in the polymer matrix.

While the following is referenced principally to the use of the preferred cellulose ester, cellulose acetate, it is understood that other cellulose esters such as cellulose propionate, cellulose acetate butyrate, and the like, can also be employed as the herbicide carrier.

The cellulose acetate herein is soluble in such common organic solvents as ketones, esters and other known and conventional cellulose acetate solvents. Thus, for example, cellulose acetate can be dissolved in a suitable ketone solvent such as acetone, methyl ethyl ketone, 2-pentanone, 3-pentanone, 2-hexanone, 3-hexanone, methyl isobutyl ketone, cyclohexanone, acetophenone, benzophenone, an ester such as ethyl acetate, ethyl propionate, ethyl butyrate, ethyl isobutyrate, propyl acetate, propyl butyrate, butyl acetate, butyl butyrate, amyl acetate or a cyclic ether such as 1,4-dioxane. Mixtures of cellulose acetate solvents can also be advantageously employed herein. The optimum amount of solvent to be used in a given operation will depend upon such factors as the characteristics of the solvent, the nature of the cellulose ester, temperature, etc., and is readily determined by those skilled in the art using routine procedures. Excellent results have been obtained with 5% and 10% by weight cellulose acetate having an acetyl value of 55 in a 60/40 weight % solution of acetone/formamide.

The addition to the cellulose acetate solution under vigorous agitation of a liquid which is a non-solvent for cellulose acetate, but miscible in the cellulose acetate solvent, will cause the cellulose acetate to separate from solution as low density, porous particles having voids, or channels, communicating with the exterior surface of the particles. Thus, for example, the addition of water or an alcohol such as methanol ethanol, propanol, isopropanol, butanol, hexanol, and the like, to an acetone/formamide solution of cellulose acetate will result in the separation of porous cellulose acetate particles in a homogeneous liquid. Water is the preferred liquid herein for reasons of economy and efficiency of operation. As will be readily appreciated by those skilled in the art, the optimum amount of water or other non-solvent used will depend upon the concentration of the cellulose ester solution, the nature of both the solvent and non-solvent, and the prevailing ambient conditions, and is readily determined employing conventional procedures.

Advantageously, the non-solvent is added to the cellulose acetate solution under high shear mixing conditions. On a laboratory scale, a Waring blender or Osterizer will provide good results. Stirring is usually of brief duration, 30 seconds providing complete separation of the cellulose acetate particles. A typical wet sieve analysis has provided cellulose acetate particles of varying particle size of which more than 80% by weight pass through a U.S. Sieve No. 20, i.e., less than 841 microns (cellulose acetate sample B of Example I, Infra).

Following the separation of the porous cellulose acetate particles from the solvent, the particles can be recovered by any suitable means, for example, by decantation, filtration, or centrifugation. If desired, the particles can be washed free of any residual coagulant liquid. In any event, following separation, the porous particles should not be permitted to dry to any appreciable extent prior to being filled with herbicide since drying results in undesirable collapse and/or constriction of the voids. The wet cellulose acetate particles are then contacted with a solution of herbicide in a non-solvent for cellulose acetate. The herbicide solvent is preferably one of good solvency so that a relatively highly concentrated solution of herbicide is imbibed by the particle voids providing high herbicide loading in the particles following drying. Organic solvent solutions of benzoic acid herbicides, e.g., methanol solutions, have provided excellent results and are preferred for use herein. When an alcohol is used as the non-solvent for the step of separating the cellulose acetate particles from solution, the herbicide can be previously dissolved in the alcohol thereby accomplishing the simultaneous separation of the cellulose acetate powder and the absorption of the herbicide into the voids of the powder. It is further within the scope of this invention to dissolve the herbicide in the cellulose acetate solvent. For example, Amiben is soluble in acetone to the extent of 23.27 gm./100 gm. at 20° C. Thus, addition of non-solvent to a cellulose acetate/herbicide solution will also result in simultaneous separation of the cellulose acetate powder and the absorption of the herbicide therein.

The amount of herbicide imbibed by the cellulose acetate particles will vary largely according to the volume of the voids in the particles and, to a lesser extent, the nature of the herbicide solvent vehicle and the duration of contact of the particles with the herbicide solution. Herbicide loadings of from about 25 to about 60% by weight are typical.

The volume of the voids in a given quantity of cellulose acetate particles is related to the amount of urea imbibed by a two or three gram sample of the particles in 100 grams of a 45/55 weight % solution of urea/distilled water over a four hour period. Such a procedure offers a simple means for evaluating the relative porosity of a cellulose acetate particle sample. Cellulose acetate particles prepared in accordance with the invention typically imbibed from about 60% to about 75% by weight of urea. Drying of the wet cellulose acetate particles can be accomplished by any suitable method, for example, by air-drying at ambient temperature or at an elevated temperature which is below the softening point of the resin and at ambient or subatmospheric pressures.

Following the alternative method of preparing the herbicidal composition of the invention, finely sized particles of a foreign material which is insoluble in cellulose acetate is incorporated therein. Advantageously, the foreign material is a water-leachable inorganic salt, both for reasons of economy as well as process efficiency. Thus, for example, an inorganic salt such as sodium chloride, potassium chloride, sodium carbonate, calcium chloride, and the like, of suitable particle size is substantially uniformly incorporated in a molten mass of cellulose acetate (melting point about 260° C) or an organic solvent solution of cellulose acetate, the solvent content of the latter thereafter being evaporated. Micronized salt is advantageously employed. The amount and particle size of the salt added to the cellulose acetate will be the principal factors governing the use and quantity of the voids in the cellulose acetate following the leaching step. These factors can be readily manipulated to provide cellulose acetate particles having a predetermined degree of voidness as will be understood by those skilled in the art. Prior to, or following, pulverization of the salt-containing cellulose acetate mass in a ball mill or other known and conventional pulverizing apparatus the resulting particles are leached with water to remove the salt. Leaching of pulverized cellulose acetate is preferred since the greater exposed surface of the particles will accelerate the extraction of the salt. If an alkali metal salt is used, care must be taken to insure that virtually all of the salt is leached from the cellulose acetate powder so as to avoid any alkali contamination of the soil to which the herbicide-filled powders will eventually be applied. The salt-free porous cellulose acetate powder is contacted with a herbicide solution and dried as in the above described preferred procedure for preparing the herbicidal compositions herein.

The following examples are illustrative of the herbicide-filled cellulose acetate compositions of this invention and the methods of their preparation.

EXAMPLE I (1) Preparation of Cellulose Acetate Solutions

The following cellulose acetate (acetyl value of 55) solutions are prepared using a 60/40 weight % solution of acetone/formamide as solvent:

|  | A | B | C | D | E | F |
|---|---|---|---|---|---|---|
| Weight % cellulose acetate | 10 | 10 | 5 | 20 | 10 | 10 |
| Weight % solvent | 90 | 90 | 95 | 80 | 90 | 90 |
| Blending time (hours) | 16 | 16 | 16 | 16 | 18-1/4 | 17-1/6 |

(2) Preparation of Porous Cellulose Acetate Particles

These solutions (in separate runs) are each injected under pressure through a Jamesbury valve, through a Monofil jet and into an Osterizer blender set at "blend". The conditions are recorded as follows:

|  | Cellulose Acetate Particles*** | | | | |
|---|---|---|---|---|---|
|  | A | B | C | D | G** |
| Cellulose acetate sol. |  |  |  |  |  |
| Monofil jet, size in M | 1000 | 1000 | 400 | 1000 | 1000 |
| Dropping distance | 4 in. | 4 in. | 4 in. | 4 in. | 4 in. |
| Amt. of distilled water in Osterizer | 2¼ cups | 2¼ cups | 2¼ cups | 2¼ cups | 2¼ cups |
| Room temperature | 26° C | 24° C | 24° C | 24° C | 22° C |
| Osterizer setting | blend | blend | blend | blend | blend |
| Delivery time | 20 sec. | 20 sec. | 20 sec.* | 20 sec. | 20 sec. |
| Nitrogen pressure | 20 psig | 20 psig | 20 psig | 20 psig | 20 psig |
| No. of washes on Buchner funnel | 2 | 2 | 2 | 2 | 2 |

-continued

| | Cellulose Acetate Particles*** | | | | |
|---|---|---|---|---|---|
| Amt. of distilled water, each wash | 2¼ cups | 2¼ cups | 2¼ cups | 2¼ cups | 2¼ cups |

*The cellulose acetate solution in the jet continued to fall after the valve was closed.
**Combination of cellulose acetate solutions E and F - procedure carried out in six equal portions.
***The total amount of each cellulose acetate solution is 300 ml prepared in 50 ml portions.

(3) Wet Sieve Analysis of Porous Cellulose Acetate Particles

Wet cellulose acetate particle samples B and G were sieved with the following results:

| U.S. Sieve | | Wt. % Retained on Sieve | |
|---|---|---|---|
| No. | Microns | B | G |
| 230 | 63 | 0.3 | 0.1 |
| 200 | 74 | 0.3 | 0.1 |
| 140 | 105 | 0.4 | 0.1 |
| 100 | 149 | 1.3 | 1.0 |
| 60 | 250 | 1.7 | 2.3 |
| 40 | 420 | 24.4 | 7.8 |
| 30 | 595 | 50.2 | 12.0 |
| 20 | 841 | 21.5 | 77.0 |

(4) Preparation of Herbicide-Filled Cellulose Acetate Particles

Cellulose acetate particle samples B, C and G were contacted with methanol solutions of Amiben and Banvel and following a period of imbibition with occasional stirring, were dried. The procedure employed is summarized as follows:

| | Herbicide-Filled Cellulose Acetate Particles | | | | | |
|---|---|---|---|---|---|---|
| (Wet) cellulose particles | B* | C* | G* | G** | G** | G** |
| Weight % Herbicide in methanol | 15 | 10 | 10 | 15 | 7.5 | 15 |
| Weight (grams) methanol herbicide sol. | 100 | 100 | 300 | 100 | 100 | 200 |
| Weight (grams) cellulose acetate particles | 15 | 15 | 75 | 20 | 20 | 40 |
| Period of imbibition (hours) | 2.0 | 4.0 | 4.0 | 4.0 | 4.0 | 4.0 |
| Weight % herbicide imbibed*** | 47.8 | 37.2 | 49.36 | 55.04 | 26.61 | 32.49 |

*Amiben
**Banvel
***As measured from % absorbance of 1,4-dioxane solution of herbicide filled particles using I. R. spectrophotometry.

EXAMPLE II

A 10% by weight solution of cellulose acetate in a 60 weight % solution of acetone is prepared. 35 grams of micronized sodium chloride (60 mesh) is added to 150 ml. of the cellulose acetate solution and the mixture is vigorously stirred in an Osterizer blender and quickly cast as a 16 mil thick film. After air drying, the film is ground to a powder (10–20 mesh) in a ball mill.

The powder is then leached with distilled water to dissolve the salt content thereof. The wet salt-free powder is contacted with a 10% by weight methanol solution of Banvel herbicide. After four hours of occasional stirring, the powder is recovered by filtration and air dried.

EXAMPLE III

The controlled release of herbicide from Amiben-filled cellulose acetate particles prepared in accordance with this invention and measured as resistance to water leaching is determined as follows:

Filter paper is placed in a 10 cm. diameter Buchner funnel, 135 ml. of dry sand mixed with Amiben-filled cellulose acetate powder containing the equivalent of 20 mg. of Amiben is placed on the filter paper, a second sheet of filter paper is placed on the sand/herbicide mixture and 40 ml. of dry sand are placed on the second sheet of filter paper. The sand is extracted with 180 ml. portions of distilled water, each portion being equivalent to approximately 1 inch of rainfall. The separate extracts are analyzed by an appropriate method for Amiben. After 10 extractions, the sand and its components are transferred to a beaker and are digested with 1,4-dioxane to dissolve the polymer. The 1,4-dioxane is evaporated or made up to a known volume to be analyzed for unleached active ingredient.

The identical procedure was repeated except that 20 mg. of Amiben was employed in place of the Amiben-filled cellulose acetate powder. The following results were recorded:

| Average Particle Size (Mesh) | % Leached, 10 Inch Rainfall Equivalent | |
|---|---|---|
| | Amiben Control | Amiben-filled Cellulose Acetate |
| 10–20 | 72,64 | |
| 10–20 | | 38,25 |

EXAMPLE IV

The controlled release of herbicide from Amiben-filled cellulose acetate particles (40% by weight herbicide) prepared in accordance with this invention and measured by bioassay is determined as follows:

A 90% sand mix was prepared by blending sand and a standard greenhouse compost. The Amiben-filled cellulose acetate powder was mixed into various portions of the sand at levels of 5, 2.5 and 1.25 lbs./acre: Other portions were treated with Amiben at the same levels. Untreated sand was maintained as a control. The soils, containing Miracle-Gro fertilizer (to correct nutrient deficiencies), were treated with water equivalent to 1 inch of rainfall and after 72 hours, sown with morning glory, mustard, foxtail millet, Japanese millet, crabgrass and velvet leaf. Visual examination of the post-emergence soils revealed a distinctly superior herbicidal performance for the compositions of this invention at all treatment levels.

In referring to voids, or channels formed in the cellulose ester structures defined herein, it is intended to comprehend pores, passageways or other internal structure contributing to surface area and the capacity of the structure to entrain, imbibe or occlude the herbicide, without limitation.

Reference has been made herein to the benzoic acid herbicides which are in some cases available in salt form, e.g., as the ammonium salt whereas the present disclosure should be considered confined essentially to these herbicides employed as the free acids.

The herbicidal component will be provided to the soil over an extended term of e.g. three to six weeks or more in an effective amount for the control of undesirable plant species such as annual broad leaf and grass weeds in accordance with recommended dosage limits therefor, in respect of use in conjunction with specified cultivars such as small grains, corn, flax, perennial seed grasses, turf, as well as non-crop lands. The compositions of the invention may be applied to the surface or incorporated into the soil in conventional manner.

What is claimed is:

1. A controlled-release herbicidal composition comprising discrete particles of a water-leachable benzoic acid herbicide selected from the group consisting of mono-, di- and tri- substituted benzoic acids in which the substituents are halo, amino, nitro and lower alkoxy occupying the voids, or channels, of a particulate, substantially water-impermeable, porous cellulose ester carrier, said voids, or channels, communicating with the exterior surface of the carrier particles.

2. The composition according to claim 1, wherein the cellulose ester is cellulose acetate.

3. The composition according to claim 1, wherein the herbicide is selected from the group consisting of 3-amino-2,5-dichlorobenzoic acid, 2-methoxy-3,6-dichlorobenzoic acid, trichlorobenzoic acid and 3-nitro-2,5-dichlorobenzoic acid.

4. The composition according to claim 1, wherein the concentration of herbicide is from about 35% to about 50% by weight of the cellulose ester carrier.

5. A method for preparing a controlled-release herbicidal composition which comprises:
   (a) dissolving cellulose ester in a solvent;
   (b) combining the cellulose ester solution with a sufficient amount of a liquid which is a non-solvent for cellulose ester, but miscible with the cellulose solvent, under vigorous agitation to provide a homogeneous liquid containing porous cellulose ester particles having voids, or channels, communicating with the exterior surface thereof;
   (c) contacting the cellulose ester particles with a water-leachable benzoic acid herbicide selected from the group consisting of mono-, di- and tri-substituted benzoic acids in which the substituents are halo, amino, nitro and lower alkoxy dissolved in a liquid which is a non-solvent for cellulose ester whereby the voids, or channels, of the cellulose ester particles become partially or substantially completely occupied with at least part of the herbicide solution; and
   (d) drying the cellulose ester particles.

6. The method according to claim 5, wherein the cellulose ester is cellulose acetate.

7. The method according to claim 6, wherein the cellulose acetate solvent is a mixture of acetone and formamide.

8. The method according to claim 6, wherein the non-solvent for cellulose acetate is water.

9. The method according to claim 5 wherein the herbicide is selected from the group consisting of 3-amino-2,5-dichlorobenzoic acid, 2-methoxy-3,6-dichlorobenzoic acid, trichlorobenzoic acid and 3-nitro-2,5-dichlorobenzoic acid.

10. The method of claim 5, wherein the concentration of herbicide in the dried cellulose ester powder is from about 35% to about 50% by weight of the cellulose ester.

11. A method for preparing a controlled-release herbicidal composition which comprises:
    (a) incorporating particles of a solid foreign material insoluble in cellulose ester substantially uniformly throughout a mass of cellulose ester;
    (b) pulverizing the cellulose ester mass to provide cellulose ester particles containing particles of solid foreign material distributed substantially uniformly throughout said particles;
    (c) leaching the particles of solid foreign material contained in the cellulose ester particles with a liquid which is a solvent for the foreign material but a non-solvent for the cellulose ester to provide porous cellulose ester particles having voids, or channels, communicating with the exterior surface of said particles;
    (d) contacting the cellulose ester particles with a water-leachable benzoic acid herbicide selected from the group consisting of mono-, di- and tri-substituted benzoic acids in which the substituents are halo, amino, nitro and lower alkoxy dissolved in a liquid which is a non-solvent for cellulose ester whereby the voids, or channels, of the cellulose ester particles become partially or substantially completely occupied with at least a part of the herbicide solution; and
    (e) drying the cellulose ester particles.

12. A method for preparing a controlled-release herbicidal composition which comprises:
    (a) incorporating particles of a solid foreign material insoluble in cellulose ester substantially uniformly throughout a mass of cellulose ester;
    (b) leaching the particles of solid foreign material contained in the cellulose ester mass with a liquid which is a solvent for the foreign materials but a non-solvent for the cellulose ester to provide a porous cellulose acetate mass;
    (c) pulverizing the porous cellulose ester mass to provide porous cellulose ester particles having voids, or channels, communicating with the exterior surface of said particles;
    (d) contacting the cellulose ester particles with a water-leachable benzoic acid herbicide selected from the group consisting of mono-, di- and tri-substituted benzoic acids in which the substituents are halo, amino, nitro and lower alkoxy dissolved in a liquid which is a non-solvent for cellulose ester whereby the voids, or channels, of the cellulose ester particles become partially or substantially completely occupied with at least a part of the herbicide solution; and
    (e) drying the cellulose ester particles.

13. A method for delivering an effective amount of a benzoic acid herbicide to a soil region for control of undesirable weed species in a controlled and sustained manner over a period of at least three weeks comprising providing said herbicide to the soil in the form of granules of the composition of claim 1.

* * * * *